United States Patent [19]

Pankhania et al.

[11] Patent Number: 4,839,176
[45] Date of Patent: Jun. 13, 1989

[54] THERAPEUTIC AGENTS

[75] Inventors: Mahendra G. Pankhania, Nottingham, England; Michael C. Meyer, Gwent, Wales

[73] Assignee: Boots Company PLC, Nottingham, England

[21] Appl. No.: 130,061

[22] Filed: Dec. 8, 1987

[30] Foreign Application Priority Data

Dec. 10, 1986 [GB] United Kingdom ............... 8629567

[51] Int. Cl.4 .................. A61K 9/20; A61K 31/485
[52] U.S. Cl. .................... 424/465; 514/282; 514/567; 514/568; 514/781
[58] Field of Search ............. 424/465; 514/282, 781, 514/567, 568

[56] References Cited

U.S. PATENT DOCUMENTS

| | | | |
|---|---|---|---|
| 3,792,170 | 2/1974 | Shen | 514/568 |
| 3,936,528 | 2/1976 | Katz | 514/282 |
| 4,083,981 | 4/1978 | Yamamoto et al. | 514/282 |
| 4,156,002 | 5/1979 | Brown | 514/245 |
| 4,176,194 | 11/1979 | Waring | 514/567 |
| 4,205,087 | 5/1980 | Waring | 514/571 |
| 4,254,122 | 3/1981 | Brown | 514/245 |
| 4,361,580 | 11/1982 | Peck et al. | 514/560 |
| 4,379,789 | 4/1983 | Capetola et al. | 514/282 |
| 4,404,210 | 9/1983 | Schmidt | 514/282 |
| 4,439,453 | 3/1984 | Vogel | 514/781 |
| 4,464,376 | 8/1984 | Sunshine et al. | 424/253 |
| 4,489,080 | 12/1984 | Lomen | 514/282 |
| 4,552,899 | 11/1985 | Sunshine et al. | 514/568 |
| 4,558,051 | 12/1985 | Sunshine et al. | 514/282 |
| 4,571,400 | 2/1986 | Arnold | 514/282 |
| 4,587,252 | 5/1986 | Arnold | 514/282 |
| 4,609,675 | 9/1986 | Franz | 514/781 |

FOREIGN PATENT DOCUMENTS

| | | |
|---|---|---|
| 68838 | 1/1983 | European Pat. Off. |
| 159852 | 10/1985 | European Pat. Off. |
| 172014 | 2/1986 | European Pat. Off. |
| 185420 | 6/1986 | European Pat. Off. |
| 220805 | 6/1987 | European Pat. Off. |
| 845785 | 3/1985 | South Africa |
| 2021413 | 12/1979 | United Kingdom |

OTHER PUBLICATIONS

Journal of Human Pharmacology and Drug Thereapy, 5/16/82, vol. 2, No. 3., pp. 162–167.
Analgesic Efficacy of 2-Ibuprofen/Codein Combinations, etc., Clin. Phar. Ther., vol. 42, No. 4, Oct. 1979, pp. 374–380.

*Primary Examiner*—Shep K. Rose
*Attorney, Agent, or Firm*—Doanld A. Peterson; Herbert D. Hart, III

[57] ABSTRACT

A solid storage stable composition comprising ibuprofen or a pharmaceutically acceptable salt thereof and codeine or a pharmaceutically acceptable salt thereof together with a sufficient amount of a pharmaceutically acceptable insoluble salt of carboxymethylcellulose to prevent discoloration of the composition.

12 Claims, No Drawings

4,839,176

THERAPEUTIC AGENTS

FIELD OF THE INVENTION

This invention relates to pharmaceutical compositions comprising ibuprofen or a pharmaceutically acceptable salt thereof and codeine or a pharmaceutically acceptable salt thereof and a pharmaceutically acceptable insoluble salt of carboxymethylcellulose, which are stable on storage.

BACKGROUND OF THE INVENTION

DESCRIPTION OF THE RELATED ART

Ibuprofen, the chemical name of which is 2-(4-isobutylphenyl)propionic acid, is a well-known medicament with anti-inflammatory, antipyretic and analgesic activities. The uses of ibuprofen include the treatment of pain and inflammation in muscoskeletal disorders such as rheumatic disease and the treatment of pain in a variety of other disorders, for example headache, neuralgia and dysmenorrhoea.

Codeine, the chemical name of which is 7,8-didehydro-4,5-epoxy-3-methoxy-17-methylmorphinan-6-ol, is also a well-known medicament and has analgesic, narcotic, antispasmodic and antitussive activities.

On some occasions it is advantageous to provide a formulation containing a combination of ibuprofen and codeine, for example in the treatment of post-operative pain, dysmennorhoea, pain due to trauma, e.g. sprains, and post-extraction dental pain (see for example Cooper et al, Journal of Human Pharmacology and Drug Therapy, 1982, volume 2, number 3, p.162–167). It has been found however, that the storage properties of pharmaceutical compositions comprising an admixture of ibuprofen and codeine are generally unsatisfactory. This is most clearly seen in a tablet where, after a short period of time, the tablet presentation becomes unacceptable. This may take the form of discolouration, expansion or cracking of the tablet which may eventually lead to the break up of the tablet. Excipients which may be incorporated in typical dosage forms include one or more of binders, diluents, disintegrants, lubricants or stabilisers. The degree of discolouration, cracking or expansion may vary according to the choice and amounts of excipients used to form the composition. Some systems of excipients and active ingredients interact to a greater extent than others. It has been observed, for example that when well-known disintegrants such as cross-linked polyvinylpyrrolidones, croscarmellose sodium, maize starches, sodium starch glycollate and a commercially available mixture of 17% protein and 80% high molecular weight polysaccharide, sold under the trade name Emcosoy, are incorporated in solid compositions comprising ibuprofen and codeine, a satisfactory storage stability is not achieved. In particular, the appearance and form of a tablet containing ibuprofen, codeine and the above-mentioned disintegrants becomes unacceptable after a short period of time.

The problem of interaction is addressed in European Patent Application 159852, with particular emphasis on the problem of providing a satisfactory pharmaceutical composition containing codeine or its salts and other non-steroidal analgesics (including ibuprofen), as interaction causes discolouration of the product and adversely affects the stability of the active ingredients. A multi-stage process is disclosed in EP 159852A which minimises contact between the active ingredients in order to improve the stability of the resulting product. The process comprises blending one of the active ingredients with a binder and a filler;
wet granulating the mixture so produced in the presence of a solvent;
drying the granulated mixture;
sizing the granulated mixture; and
blending the mixture with one or more other pharmaceutically active ingredients.

SUMMARY OF THE INVENTION

Unexpectedly, it has now been found that when insoluble salts of carboxymethylcellulose are incorporated in a solid composition comprising ibuprofen and codeine, the composition is stable on storage. Calcium carboxymethylcellulose is a known disintegrant. The above discovery, however, is surprising in view of the instability of ibuprofen/codeine compositions containing other well-known disintegrants.

An object of the invention is to provide an ibuprofen/codeine composition which is stable on storage and which does not involve complex formulation stages.

Accordingly, in one broad form the present invention includes a solid storage stable composition comprising ibuprofen or a pharmaceutically acceptable salt thereof and codeine or a pharmaceutically acceptable salt thereof, together with a sufficient amount of a pharmaceutically acceptable insoluble salt of carboxymethylcellulose to prevent discolouration of the composition.

The present invention also includes a solid storage stable composition in unit dosage form to relieve an inflammatory condition or to provide an analgesic effect in a subject.

The present invention also includes a method of effecting analgesia in a mammalian subject, including humans and animals, which comprises administering to said subject in need thereof an analgesically effective amount of an admixture of ibuprofen or a pharmaceutically acceptable salt thereof and codeine or a pharmaceutically acceptable salt thereof and a sufficient amount of a pharmaceutically acceptable insoluble salt of carboxymethylcellulose to prevent discolouration of said admixture.

The present invention also includes a method of treating inflammation in a mammalian subject, including humans and animals, which comprises administering to said subject having an inflammatory condition an anti-inflammatory effective amount of an admixture of ibuprofen or a pharmaceutically acceptable salt thereof and codeine or a pharmaceutically acceptable salt thereof and a sufficient amount of a pharmaceutically acceptable insoluble salt of carboxymethylcellulose to prevent discolouration of said admixture.

Also included as a part of the invention is a process to prepare a composition having minimal discolouration on storage wherein ibuprofen or a pharmaceutically acceptable salt thereof is combined with codeine or a pharmaceutically acceptable salt thereof together with a sufficient amount of a pharmaceutically acceptable insoluble salt of carboxymethylcellulose to prevent discolouration of the composition, to form a uniform mixture and optionally compressing the mixture to form a tablet.

DETAILED DESCRIPTION OF THE INVENTION AND SPECIFIC EMBODIMENTS

It has been found that composition comprising ibuprofen, codeine and a pharmaceutically acceptable, non-toxic, insoluble salt of carboxymethylcellulose are stable on storage. In particular it has been found that compositions in tablet form do not suffer from discolouration on storage and also do not expand and crack or split which would cause the table to break up. It has also been observed that there is no degradation of either the ibuprofen or the codeine, accordingly the compositions retain their therapeutic activity. Furthermore, the incorporation of insoluble salts of carboxymethylcellulose in the composition does not add significantly to the overall formulation cost as the salt may also function effectively in the composition as a disintegrant. In addition, this dual function provides that the insoluble salt of carboxymethylcellulose does not add substantially to the bulk of the compositions. Normally sodium metabisulphite must be added to compositions containing codeine in order to achieve satisfactory chemical stability. A further advantage of the invention lies in the finding that it is not necessary to add sodium metabisulphite to these compositions, particularly as sulphites have been found to provoke reactions in certain susceptible people. In addition, the compositions provided according to the invention are observed to have satisfactory disintegration and dissolution properties.

It will be appreciated that reference herein to ibuprofen and codeine includes a reference to the pharmaceutically acceptable salts of ibuprofen and codeine respectively. The preferred combination of active ingredients in compositions according to the invention is ibuprofen and codeine phosphate. The pharmaceutically acceptable insoluble salt of carboxymethylcellulose is preferably the calcium salt. Calcium carboxymethylcellulose is described in the 1985 U.S. National Formulary, (US NF), volume XVI, p1542-3, as the calcium salt of a polycarboxymethylether of cellulose. Calcium carboxymethylcellulose may be prepared from cellulose, ie cellulose is carboxymethylated and the product is then converted to the calcium salt.

The pharmaceutically acceptable insoluble salt of carboxymethylcellulose is added to the composition to enhance the stability of the combination of active ingredients. In particular it is added in a sufficient quantity to avoid or minimize discolouration of the compositions, particularly those in tablet form. Conveniently the composition according to the invention comprises 1-40% by weight of an insoluble salt of carboxymethylcellulose, preferably 5-20%, advantageously 7-12% by weight. In a preferred composition according to the invention calcium carboxymethylcellulose is incorporated to an extent of 8 to 10% by weight of the composition.

Conveniently the ratio of the insoluble salt of carboxymethylcellulose to ibuprofen is in the range 1:2 to 1:10, preferably 1:3 to 1:9 parts by weight and suitably the ratio of the insoluble salt of carboxymethylcellulose to codeine is 1:0.1 to 1:2, preferably 1:0.2 to 1:1, parts by weight. In valuable compositions 0.5 to 10 parts by weight calcium carboxymethylcellulose are used per part by weight codeine. Preferred compositions comprise the ingredients in the ratio of 0.5 to 1.5 parts by weight calcium carboxymethylcellulose, 4 to 8 parts by weight ibuprofen and 0.4 to 1.0 parts by weight codeine phosphate.

The ibuprofen and codeine may be present in the composition to the extent desired for therapeutic effectiveness. Suitably 50-1200 mg ibuprofen may be present, preferably 200-800 mg. The dosage as employed for an adult human treatment is generally in the range from 150 to 3600 mg ibuprofen per day. Codeine may be added to the composition to an extent of 100 mg, for example 10-100 mg, preferably 30-60 mg. The dosage as employed for an adult human treatment is generally in the range 30-300 mg codeine per day. Valuable compositions comprises 10-90% by weight ibuprofen, especially 30-80% by weight. Preferably the composition comprises 1 to 15% by weight of codeine, especially 2 to 10% by weight. Advantageous compositions comprise 50 to 70% by weight ibuprofen and 4 to 10% by weight codeine, in particular codeine phosphate and 8 to 10% by weight calcium carboxymethyl-cellulose.

The solid composition is preferably presented in the form of a tablet, however advantages may also be obtained by the incorporation of an insoluble salt of carboxymethylcellulose in other solid dosage compositions such as powder-filled and paste-filled capsules, lozenges, and compressed suppositories and pessaries.

Other formulation excipients may also be incorporated into a composition according to the invention. Such pharmaceutically acceptable excipients may be added to modify the rate of drug dissolution and/or facilities the manufacture of suitable dosage forms of the formulation. Suitable excipients which may be added include binders, soluble and insoluble diluents, stabilisers, lubricants, flow aids, oils, fats and waxes as desired.

Examples of binders include polyvinylpyrrolidone, microcrystalline cellulose, gelatin and gums. In general binders may comprise up to 20% by weight of the composition. Examples of soluble diluents include lactose, sodium chloride, dextrins and sorbitol and examples of insoluble diluents include microcrystalline cellulose, calcium sulphate and di- and tri- calcium phosphate. Diluents may be used by up to 50% by weight of the composition. Also there may be added to the composition up to 5% by weight of lubricants, for example stearic acid, polyethylene glycol 6000, magnesium stearate; up to 5% by weight of flow aids such as colloidal silica and talc. Surfactants, e.g. sodium lauryl sulphate and Tween 80, flavourings and other oils, fats and waxes may be added as desired in small amounts.

If desired, the solid dosage form may be coated with any conventional coating material. In particular, tablets may be coated with a film coating.

A composition according to the invention may be prepared by formulating ibuprofen, codeine and an insoluble salt of carboxymethylcellulose, together with other optional tabletting excipients in the normal way, for example by combining all the ingredients by mixing in a rotating drum to form a uniform mixture, optionally followed by compression into tablets.

It will be appreciated that compositions according to the invention are particularly useful as analgesics and anti-inflammatory agents.

The invention is illustrated by the following non-limitative examples.

In the Examples, the ibuprofen is available from the Boots Company, Nottingham, England; codeine phosphate is available from The Boots Company or from McFarlan Smith, Edinburgh, Scotland; calcium carboxymethylcellulose is available from Carnation Gums, London, England under the trade name ECG 505; the microcrystalline cellulose is available from FMC Corporation, Philadelphia, USA under the trade name Avicel PH101; the fumed silica is available from Degussa, West Germany under the trade name Aerosil 200; and the polyvinylpyrrolidone is available from GAF (GB) Limited, Manchester, England under the trade name Plasdone K29-32;

EXAMPLE 1

Tablets containing 400 mg ibuprofen and 30 mg codeine phosphate

| Ingredient | Quantity % w/w |
|---|---|
| Ibuprofen | 57.14 |
| Microcrystalline cellulose (Avicel PH101) | 26.82 |
| Calcium carboxymethylcellulose (ECG 505) | 10.00 |
| Fumed Silica (Aerosil 200) | 0.50 |
| Codeine Phosphate BP | 4.30 |
| Stearic Acid BPC | 0.50 |
| Sodium Metabisulphite BP | 0.04 |
| Polyvinylpyrrolidone (Plasdone K29-32) | 0.70 |

Ibuprofen, the microcrystalline cellulose, 21% of the calcium carboxymethylcellulose and 50% of the fumed silica were granulated using a solution of the polyvinylpyrrolidone in isopropyl alcohol. The granules were then sized and dried to remove the isopropyl alcohol. The dry granulate was sized and blended with the remaining excipients and compressed into tablets using suitable tooling.

There was found to be no discolouration and no cracking or splitting of the tablets on storage for five years either:
(a) at ambient temperature; or
(b) at 30° C. and 80% relative humidity.

EXAMPLE 2

Tablets containing 200 mg ibuprofen and 15 mg codeine phosphate were prepared using the same proportions of ingredients as described in Example 1.

There was found to be no discolouraton and no cracking or splitting of the tablets on storage for five years either:
(a) at ambient temperature; or
(b) at 30° C. and 80% relative humidity.

EXAMPLE 3

Tablets containing 400 mg ibuprofen and 60 mg codeine phosphate

| Ingredient | Quantity % w/w |
|---|---|
| Ibuprofen | 57.14 |
| Microcrystalline cellulose (Avicel PH101) | 22.48 |
| Calcium carboxymethylcellulose (ECG 505) | 10.00 |
| Fumed silica (Aerosil 200) | 0.50 |
| Codeine Phosphate BP | 8.60 |
| Stearic Acid BPC | 0.50 |
| Sodium Metabisulphite BP | 0.08 |
| Polyvinylpyrrolidone (Plasdone K29-32) | 0.70 |

The tablets were prepared in a similar way as described in Example 1.

There was found to be no discolouration and no cracking or splitting of the tablets on storage for five years either:
(a) at ambient temperature; or
(b) at 30° C. and 80% relative humidity.

EXAMPLE 4

Tablets containing 200 mg ibuprofen and 30 mg codeine phosphate were prepared using the same proportions of ingredients as described in Example 3.

There has been found to be no discolouration nor any cracking or splitting of the tablets to date on tablets stored 12 months ago (a) at ambient temperature and (b) at 30° C. and 80% relative humidity.

EXAMPLE 5

Tablets containing 400 mg ibuprofen and 60 mg codeine phosphate

| Ingredient | Quantity % w/w |
|---|---|
| Ibuprofen | 57.2 |
| Microcrystalline cellulose (Avicel PH101) | 22.50 |
| Calcium carboxymethylcellulose (ECG 505) | 10.00 |
| Fumed silica (Aerosil 200) | 0.50 |
| Codeine Phosphate BP | 8.6 |
| Stearic Acid BPC | 0.5 |
| Polyvinylpyrrolidone (Plasdone K29-32) | 0.7 |

The tablets were prepared in the same way as described in Example 1.

There has been found to be no discolourisation nor any cracking or splitting of the tablets to date on tablets stored 12 months ago (a) at ambient temperature and (b) at 30° C. and 80% relative humidity.

Comparison

The appearance of tabletted ibuprofen/codeine compositions containing calcium carboxymethylcellulose after storage was compared with other tabletted ibuprofen/codeine compositions containing other disintegrants listed below:

Cross-linked polyvinylpyrrolidone
Croscarmellose sodium
Sodium starch glycollate
Ion Exchange resin (Amberlite IRP-88)
Maize starch
Protein and polysaccharide (17:80) [Emcosoy]

Tabletted compositions according effective levels of the listed disintegrants were stored at 50° C. and observed regularly for discolouration and for swelling or splitting. Only compositions containing calcium carboxymethylcellulose gave satisfactory results and all other formulations showed unsatisfactory storage properties due to one or more of discolouration, swelling or splitting within a 12 week period.

I claim:

1. A solid storage stable composition consisting essentially of ibuprofen or a pharmaceutically acceptable salt thereof in an amount of 10 to 90% by weight of the composition, codeine or a pharmaceutically acceptable salt thereof in an amount of 10 to 15% by weight of the composition and calcium caboxymethylcellulose in an amount of 0.5 to 10 parts by weight per part by weight codeine or the salt thereof, said amount of calcium carboxymethylcellulose being sufficient to prevent discoloration of the composition.

2. A composition according to claim 1 wherein the composition contains 5 to 20% by weight of calcium carboxymethylcellulose.

3. A composition according to claim 1 wherein the ratio of calcium carboxymethylcellulose to ibuprofen or a pharmaceutically acceptable salt thereof is in the range 1:3 to 1:9 parts by weight.

4. A composition according to claim 1 wherein the ratio of calcium carboxymethylcellulose to codeine or a pharmaceutically acceptable salt thereof is in the range 1:2 to 1:10 parts by weight.

5. A composition according to claim 1 containing 0.5 to 1.5 parts by weight calcium carboxymethylcellulose, 4 to 8 parts by weight ibuprofen and 0.4 to 1.0 parts by weight codeine or a pharmaceutically acceptable salt thereof.

6. A composition according to claim 1 containing 30 to 80% by weight of the composition ibuprofen or a pharmaceutically acceptable salt thereof.

7. A composition according to claim 1 containing 2 to 10% by weight of the composition codeine or a pharmaceutically acceptable salt thereof.

8. A composition according to claim 1 containing 50 to 70% by weight of the composition ibuprofen, 4 to 10% by weight of the composition codeine or a pharmaceutically acceptable salt thereof and 8 to 10% by weight of the composition calcium carboxymethylcellulose.

9. A composition accordign to claim 1 in the form of a tablet.

10. A process for preparing a solid storage stable composition as claimed in claim 1 comprising combining ibuprofen or a pharmaceutically acceptable salt thereof and codeine or a pharmaceutically acceptable salt thereof with calcium carboxymethylcellulose, to form a uniform mixture and optionally compressing the mixture to form a tablet.

11. A solid, storage stable, pharmaceutical ibuprofen composition in unit dosage form to relieve an inflammatory condition or to provide an analgesic effect in a subject, which consists essentially of 50 to 1200 mg ibuprofen or a pharmaceutically acceptable salt thereof, 10 to 100 mg codeine or a pharmacèutically acceptable salt thereof and 0.5 to 10 parts by weight calciuim carboxymethylcellulose per part by weight codeine or the salt thereof.

12. An ibuprofen composition according to claim 11 in the form of a compressed tablet.

* * * * *

UNITED STATES PATENT AND TRADEMARK OFFICE
CERTIFICATE OF CORRECTION

PATENT NO. : 4,839,176

DATED : June 13, 1989

INVENTOR(S) : Pankhania et al.

It is certified that error appears in the above-identified patent and that said Letters Patent is hereby corrected as shown below:

Column 6, line 58 (claim 1), after "of" and before "to" delete "10" and insert --1--.

Signed and Sealed this

Fourth Day of September, 1990

Attest:

HARRY F. MANBECK, JR.

Attesting Officer

Commissioner of Patents and Trademarks